United States Patent [19]
Baziard-Mouysset et al.

[11] Patent Number: 5,691,340
[45] Date of Patent: Nov. 25, 1997

[54] BENZOPYRAN DERIVATIVES

[75] Inventors: Geneviève Baziard-Mouysset; Sallouma Younes; Youssef Labssita, all of Toulouse; Marc Payard, Balma; Daniel-Henri Caignard, Paris; Pierre Renard, Versailles; Marie-Claire Rettori, Courbevoie, all of France

[73] Assignee: Adir et Compagnie, Courbevoie, France

[21] Appl. No.: 528,251

[22] Filed: Sep. 14, 1995

[30] Foreign Application Priority Data

Sep. 15, 1994 [FR] France .................. 94 10987

[51] Int. Cl.$^6$ .................. A61K 31/495; C07D 405/06
[52] U.S. Cl. .................. 514/253; 514/255; 544/376; 544/391; 544/398
[58] Field of Search .................. 544/376; 514/253

[56] References Cited

U.S. PATENT DOCUMENTS

| | | | |
|---|---|---|---|
| 3,470,185 | 9/1969 | Huebner et al. | 544/376 |
| 4,728,650 | 3/1988 | Eziri et al. | 514/253 |
| 4,977,166 | 12/1990 | Hardy et al. | 544/376 |
| 5,364,867 | 11/1994 | DeHaven-Hudkins | 514/326 |
| 5,519,023 | 5/1996 | Payard et al. | 544/376 |
| 5,550,129 | 8/1996 | Nöldner et al. | 514/253 |

FOREIGN PATENT DOCUMENTS

| | | |
|---|---|---|
| 0 076 996 | 4/1983 | European Pat. Off. |
| 2 157 424 | 5/1973 | Germany . |
| 94-08985 | 4/1994 | WIPO .................. 544/376 |

OTHER PUBLICATIONS

Weiner et al Behavioural Pharmacology 6, 46–54 (1995).
Sanchez et al Society for Neuroscience Abstracts, 20, 385 (1994).
Leonard European Neuropsychopharmacology, 4(3), 174–175 (1994).
Okuyama et al Life Sciences 55(7), PL 133–138 (1994).
Gerwitz et al, *Neuropsychopharmacology* 10, pp. 37–40 (1994).
Jacobsen et al, *J. Med. Chem.* 35 pp. 4464–4472 (1992).
Grisar et al, *J. Med. Chem* 38 pp. 453–458 (Feb. 1995).

*Primary Examiner*—Emily Bernhardt
*Attorney, Agent, or Firm*—The Firm of Gordon W. Hueschen

[57] ABSTRACT

A compound selected from those of formula (I):

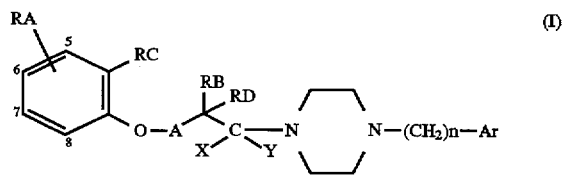

where RA, RB, RC, RD, A, n, X, Y and Ar are defined in the description, and a medicinal product comprising the same for treating a mammal afflicted with a disease associated with sigma receptors.

6 Claims, No Drawings

BENZOPYRAN DERIVATIVES

The present invention relates to new benzopyran derivatives containing a piperazine structure as well as to their process of preparation and to the pharmaceutical compositions which contain them.

Aminomethylchromans are known in the literature (Indian Journal of Chemistry, 1981, 20 B, 1063–1067 and 1982, 21 B, 344–347). The only derivatives with a piperazine structure described in these documents are phenylpiperazine derivatives. Some are mentioned as possessing properties depressive on the central nervous system. Research into the mechanism of their activity has shown these compounds with a phenylpiperazine structure had a high affinity for serotonin and dopamine receptors. The central activity of such substances is accompanied by serious side effects such as, among the most frequent, sedation, sleepiness or, more seriously, acute paroxysmal accidents: such as buccolingual spasms and oculogyric crises which are a great nuisance to the patient.

The compounds of the present invention, which have an arylalkylpiperazinoalkylbenzopyran structure, and their derivatives, in contrast have no affinity either for serotonin receptors or for dopamine receptors but have a selective affinity, of very high level, for sigma receptors. This profile makes the compounds of the invention useful in disorders of the central nervous system, as they do not have the side effects encountered in the products of the prior art. The compounds of the invention are also useful in the prevention and the treatment of diseases involving sigma receptors. In particular, they are useful in the prevention and treatment of cerebral circulatory diseases, of disorders of the memory and of Alzheimer's disease, of inflammatory diseases of immune origin, such as arthritis, and of disorders of intestinal peristalsis. More particularly, the present invention relates to the derivatives of formula (I):

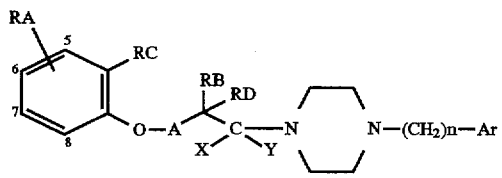

(I)

in which

Ar represents a phenyl, naphthyl, substituted phenyl or substituted naphthyl group, n represents an integer between 1 and 4 inclusive, RB represents an alkyl group, and in this case A represents a single bond and RA and RC, which are identical or different, represent, independently of one another, a hydrogen atom or a group chosen from halogen, alkyl, alkyl substituted by one or a number of halogens, and alkoxy, or RB and RC together form a —(CH$_2$)$_q$— bridge with q having the value 0, 1 or 2 and, in this case, A represents a —(CH$_2$)$_p$— bridge with p representing 0, 1 or 2 and such that p+q=1 or 2, and in this case RA represents a hydroxyl or alkoxy group situated in the 5-position of the aromatic ring which carries it or RA represents a hydrogen or halogen atom, in any position on the aromatic ring, or RB and RC together form a —CH= bridge, and the bond which bonds it to the aromatic ring is single, and in this case A represents a CH$_2$ group and RA represents a hydrogen atom or a hydroxyl or alkoxy group situated in the 5-position of the aromatic ring which carries it, or RB and RC together form a single bond and then A represents a group

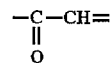

the carbonyl being bonded to the oxygen and the bond connecting A to the carbon carrying the side chain is double, and in this case RA represents a hydrogen atom or a hydroxyl or alkoxy group, when RB represents an alkyl group, X and Y each represent two hydrogen atoms or form, together with the carbon atom which carries them, a C=O group, and RD represents a hydrogen atom or an alkyl group, when RB and RC form a bridge, X and Y each represent two hydrogen atoms and RD, which only exists when all the bonds of the carbon which carries it are single, represents a hydrogen atom, it being understood that, except when otherwise mentioned, the terms "alkyl" and "alkoxy" denote linear or branched saturated groups containing from 1 to 6 carbon atoms, the term "substituted" concerning the phenyl and naphthyl substituents means that the latter can be substituted by one to three groups chosen from hydroxyl, alkyl, alkyl substituted by one or a number of halogens, alkoxy and halogen, to their optical isomers in the pure form or in the form of a mixture, and to their addition salts with a pharmaceutically acceptable acid or base.

The invention particularly relates to the compounds of formula (I) in which, taken together or separately, RA represents a hydrogen atom, RA represents a halogen atom, RA represents a hydroxyl group, RA represents an alkoxy group, Ar represents an unsubstituted phenyl, Ar represents a substituted phenyl, Ar represents a phenyl substituted by an alkoxy group, Ar represents a naphthyl, RB represents an alkyl group and RC represents a hydrogen atom, n is equal to 1, RD represents a hydrogen, and RD represents a methyl.

The invention preferably relates to:

the compounds of formula (Ic), a specific case of the compounds of formula (I) in which RB and RC form a —(CH$_2$)$_q$— bridge with q having the value 2 and RD represents a hydrogen atom

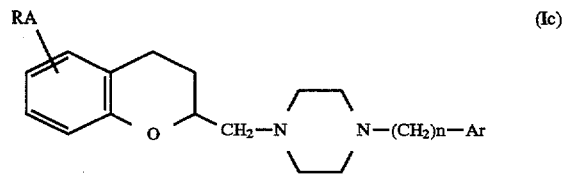

(Ic)

where RA, n and Ar have the same definition as in the formula (I), to their optical isomers in the pure form or in the form of a mixture and to their addition salts with a pharmaceutically acceptable acid or base, the compounds of formula (Id), a specific case of the compounds of formula (I) in which RB and RC form a —(CH₂)$_q$— bridge with q having the value 1, A represents CH₂ and RD a hydrogen atom,

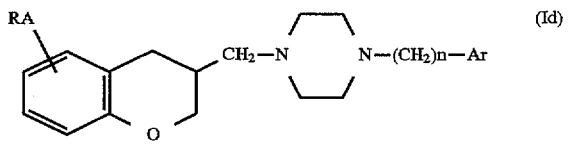

where RA, n and Ar have the same definition as in the formula (I),
to their optical isomers in the pure form or in the form of a mixture and to their addition salts with a pharmaceutically acceptable acid or base, the compounds of formula (Ie), a specific case of the compounds of formula (I) in which RB and RC form a —CH= bridge, the bond which bonds it to the carbon carrying the side chain is double and A represents a —CH₂— group,

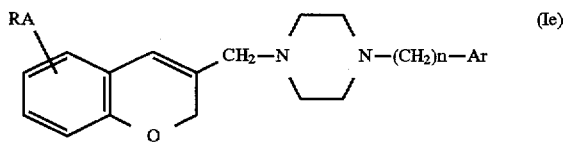

where RA, n and Ar have the same definition as in the formula (I),
to their optical isomers in the pure form or in the form of a mixture and to their addition salts with a pharmaceutically acceptable acid or base, the compounds of formula (If), a specific case of the compounds of formula (I) in which RB and RC represent a single bond and A represents a —CO—CH= linkage, the carbonyl being bonded to the oxygen,

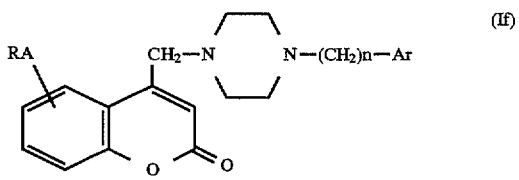

where RA, n and Ar have the same definition as in the formula (I), to their optical isomers in the pure form or in the form of a mixture and to their addition salts with a pharmaceutically acceptable acid or base, the compounds of formula (Ig), a specific case of the compounds of formula (I) in which RB represents a lower alkyl group,

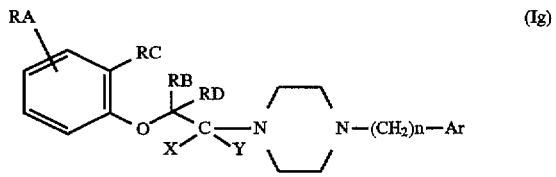

where RA, RC, RD, X, Y, n and Ar have the same definition as in the formula (I),
to their optical isomers in the pure form or in the form of a mixture and to their addition salts with a pharmaceutically acceptable acid or base, the compounds of formula (Ih), a specific case of the compounds of formula (I) in which RB and RC form a —(CH₂)$_q$— bridge with q having the value 1, RD represents a hydrogen atom and A represents a —(CH₂)$_p$— group with p having the value 0,

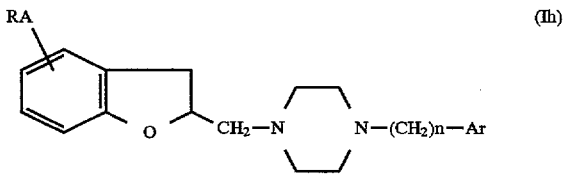

where RA, n and Ar have the same definition as in the formula (I),
to their optical isomers in the pure form or in the form of a mixture and to their addition salts with a pharmaceutically acceptable acid or base.

Specifically, the alkyl radicals present in the formula (I) can be chosen from methyl, ethyl, n-propyl, isopropyl, n-butyl, isobutyl, sec-butyl, tert-butyl, pentyl and hexyl.

The alkoxy radicals present in the formula (I) can be chosen from methoxy, ethoxy, n-propoxy, isopropoxy, n-butoxy, isobutoxy, sec-butoxy, tert-butoxy, pentyloxy and hexyloxy.

The halogens present in the formula (I) can be chosen from bromine, chlorine, fluorine and iodine.

The invention also particularly relates to the compounds of formula (I) which are:

1-[(5-fluoro-2,3-dihydrobenzofur-2-yl)methyl]-4-benzylpiperazine,

1-[(2,3-dihydrobenzofur-2-yl) methyl]-4-benzylpiperazine,

1-[(chroman-2-yl)methyl)]-4-benzylpiperazine,

1-[(7-methoxy-2H-2-oxochrom-3-en-4-yl)methyl]-4-benzylpiperazine,

1-[(7-methoxy-2H-2-oxochrom-3-en-4-yl)methyl]-4-(4-methoxybenzyl)piperazine,

1-[2-(phenoxy) propyl]-4-benzylpiperazine, to their optical isomers in the pure form or in the form of a mixture and to their addition salts with a pharmaceutically acceptable acid.

The invention also applies to the process for the preparation of the compounds of formula (I), wherein a compound of formula (II):

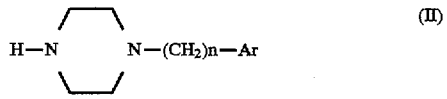

in which Ar and n are as defined in the formula (I), is reacted either with a compound of formula (III):

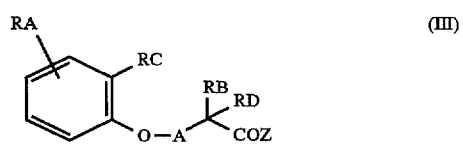

in which RA, RB, RC, RD and A are as defined in the formula (I), Z representing a hydroxyl group or a chlorine atom, in order to obtain a compound of formula (Ia):

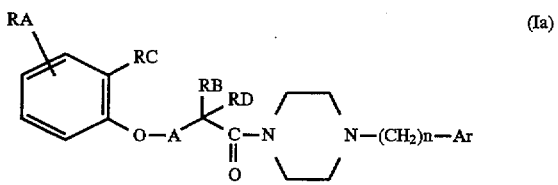

in which RA, RB, RC, RD, Ar, n and A are as defined above, which compound (Ia) can be subjected, according to the structure of the compound of formula (I) which it is desired to obtain, to a reduction to give a compound of formula (Ib):

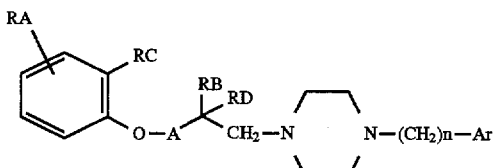

where RA, RB, RC, RD, Ar, n and A have the same definition as above, or with a compound of formula (IV) in the presence of an alkaline agent:

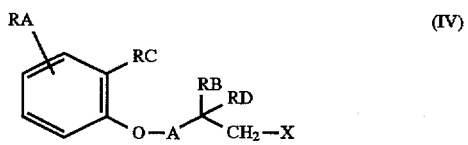

in which RA, RB, RC, RD and A are as defined above and X represents a halogen atom, in order to obtain a compound of formula (Ib) as defined above, the compounds of formula (Ia) and (Ib) forming the group of compounds of formula (I) which can be separated into their various optical isomers in the pure form or in the form of a mixture and salified with a pharmaceutically acceptable acid or base.

Mention may be made, by way of examples and without implied limitation, among the pharmaceutically acceptable acids which can be used to form an addition salt with the compounds of the invention, of hydrochloric, sulfuric, phosphoric, tartaric, malic, maleic, fumaric, oxalic, methanesulfonic, ethanesulfonic, camphoric and citric acids.

Mention may be made, by way of examples and without implied limitation, among the pharmaceutically acceptable bases which can be used to form an addition salt with the compounds of the invention, of sodium hydroxide, potassium hydroxide, triethylamine, diethylamine, ethanolamine, arginine, lysine and diethanolamine.

The starting materials used in the process described above are either commercially available or easily accessible to a person skilled in the art according to processes known in the literature.

The acid chlorides, if they are not commercially available, are obtained by treatment of the corresponding acids with a chlorinating agent, such as thionyl chloride.

The compounds of formula (I) have advantageous pharmacological properties.

The very high affinity of the derivatives of the invention for σ (sigma) receptors makes it possible to use them in the treatment of motor disorders such as dystonias (Walker J. M., Drug Specificity of Pharmacology Dystonia, Pharmacol. Biochem. Behav., 1990, 36, 151), tardive dyskinesia (Lindstrom L. H., Acta Psychiatr. Scand., 1988, 77, 1122) or psychotic disorders (Chouinard F., Annable L., Psychopharmacology, 1984, 84, 282) and of disorders such as injuries related to ischemia, cerebral circulatory insufficiency, memory disorders, Alzheimer's disease and states of shock (Pontecorvo M. J., Brain Res. Bull., 1991, 26, 461), control of immune phenomena (Carroll F. I., Med. Chem. Re., 1992, 2, 3), the treatment of addiction to cocaine (Abou-Gharbia M., Academic Press (Inc. Bristol. J. Ed. Publisher) 1993, 28, 1), the diagnosis and the localization of tumors (Hudzick T. J., Psychopharmacology, 1992, 108, 115; Abou-Gharbia M., Academic Press (Inc. Bristol. J. Ed. Publisher) 1993, 28, 1), the treatment of vomiting (Hudzick, T. J., Eur. J. Pharmacol., 1993, 236, 279), inflammatory diseases of immune origin such as arthritis, bronchopulmonary inflammation and psoriasis, allergic pathologies, eczema, septic shock and disorders of intestinal motoricity. As regards the treatment of disorders of the central nervous system, the compounds of the invention have no affinity for the central receptors other than the σ receptor and therefore do not have the side effects conventionally encountered in this type of activity.

Another subject of the present invention is the pharmaceutical compositions containing the compounds of formula (I) or one of their addition salts with a pharmaceutically acceptable acid or base, in combination with one or a number of excipients.

Mention may more particularly be made, among the pharmaceutical compositions according to the invention, of those which are suitable for oral, parenteral, nasal, per- or transcutaneous, rectal, perlingual, ocular or respiratory administration and in particular simple or sugar-coated tablets, sublingual tablets, chartulas, packets, gelatin capsules, glossettes, lozenges, suppositories, creams, ointments, dermal gels and phials to be taken orally or to be injected.

The dosage varies according to the age, sex and weight of the patient, the administration route, the nature of the therapeutic indication or possible associated treatments and ranges between 0.1 mg and 1 g per 24 hours in 1 or 2 administrations, more particularly between 1 and 100 mg, for example between 1 and 10 mg.

The following examples illustrate the invention but do not limit it in any way.

The $^1$H nuclear magnetic resonance spectra were produced using TMS (tetramethylsilane) as internal reference. The chemical shifts are expressed in parts per million (p.p.m.). The infrared spectra were recorded in the form of a potassium bromide disk containing approximately 1% of the product to be analyzed.

EXAMPLE 1

1-[(5-FLUORO-2,3-DIHYDROBENZOFUR-2-YL)METHYL]-4-BENZYLPIPERAZINE 0.03 mol of 1-[(5-fluoro-2,3-dihydrobenzofur-2-yl)carbonyl]-4-benzylpiperazine (resulting from the condensation of 5-fluoro-2,3-dihydrobenzofuran-2-carboxylic acid with N-benzylpiperazine) is dissolved in 150 ml of anhydrous tetrahydrofuran (T.H.F.). Two times 0.03 mol of lithium aluminum hydride are added in the form of pellets. The mixture is stirred at room temperature. The title compound is obtained.

Characteristics:

Molecular mass for $C_{20}H_{23}FN_2O.2HCl$: 399 g.mol$^{-1}$

Yield: 85%

$R_f$: 0.66 (Ethanol)

Melting point: 214° C.

Infrared spectroscopy (KBr, ν cm$^{-1}$):

3140–2800 (CH, CH$_2$), 2550–2440 (NH$^+$), 1620–1600 (C=C).

$^1$H Nuclear magnetic resonance (d$_6$-D.M.S.O., δ ppm):

3.01 (2 dd, 2H, C$\underline{H}_2$—CH—O: J1=9.00 Hz and J2=15.87 Hz), 3.78–3.45 (m, 12H, C$\underline{H}_2$—N$^+$, $^+$N—C$\underline{H}_2$—Ar and 8H, piperazine), 5.43 (m, $^1$H, CH$_2$—C$\underline{H}$—O), 7.77–6.84 (m, 8H, aromatic protons).

EXAMPLE 2

1-[(CHROMAN-2-YL)METHYL]-4-BENZYLPIPERAZINE

Stage A: 1[(chroman-2-yl)carbonyl]-4-benzylpiperazine

A solution of 0.01 mol of chroman-2-carboxylic acid chloride in 100 ml of methylene chloride is introduced into an Edenmeyer flask containing a solution of 0.01 mol of 1-benzylpiperazine in 100 ml of methylene chloride. The mixture is stirred for 5 hours at room temperature. The reaction is monitored by silica thin layer chromatography. After filtration, the title product is obtained in the hydrochloride form and is recrystallized from ethanol.

Characteristics:

Molecular mass for C$_{21}$H$_{24}$N$_2$O$_2$.HCl: 372.5 g.mol$^{-1}$

Yield: 52%

R$_f$: 0.77 (Ethyl acetate)

Melting point: 230° C.

Infrared spectroscopy (KBr, ν cm$^{-1}$):

3150, 3090, 3035, 2995, 2810 (CH, CH$_2$), 2600–2400 (NH$^+$), 1650 (CO), 1610 (C=C).

$^1$H Nuclear magnetic resonance (CDCl$_3$, δ ppm):

2.42 (m, 2H, CH$_2$—C$\underline{H}_2$—CH), 2.51 (m, 4H, piperazine), 2.89 (t, 2H, C$\underline{H}_2$—CH$_2$—CH), 3.52 (s, H, N-C$\underline{H}_2$—Ar), 3.82 (m, 4H, piperazine), 4.74 (m, $^1$H, O—C$\underline{H}$—CO), 6.80–7.34 (m, 9H, aromatic protons).

Stage B: 1-[(chroman-2-yl)methyl]-4-benzylpiperazine

By carrying out the preparation in the same way as in Example 1, but starting with the hydrochloride of 1-[(chroman-2-yl)carbonyl]-4-benzylpiperazine obtained in Stage A, the title compound is obtained.

Characteristics:

Molecular mass for C$_{21}$H$_{26}$N$_2$O.2HCl: 395 g.mol$^{-1}$

Yield: 93%

R$_f$: 0.55 (Ethanol)

Melting point: >230° C.

Infrared spectroscopy (KBr, ν cm$^{-1}$): 3210, 3000, 2980 (CH, CH$_2$), 2700–2200 (NH$^+$), 1605, 1590 (C=C).

$^1$H Nuclear magnetic resonance (d$_6$-D.M.S.O., δ ppm):

1.69–2.96 (m, 14H, C$\underline{H}_2$—C$\underline{H}_2$—CH—O, C$\underline{H}_2$—N, piperazine), 3.46 (s, 2H, N—C$\underline{H}_2$), 4.26 (m, 1H, CH$_2$—C$\underline{H}_2$—CH—O), 6.79–7.47 (m, 9H, aromatic protons). The 2H$^+$ protons are not visible because the product and the D.M.S.O. are hygroscopic, which implies an exchange with water.

EXAMPLE 3

1-[(7-METHOXY-2-OXOCHROM-3-EN-4-YL)METHYL]-4-BENZYLPIPERAZINE (base and hydrochloride)

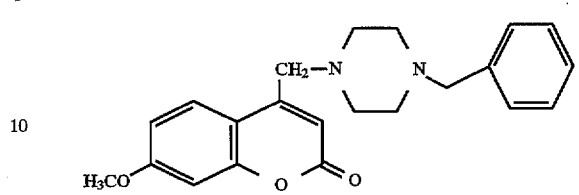

0.03 mol of 1-benzylpiperazine, 0.03 mol of 7-methoxy-2-oxo-4-bromomethyl-3-chromene and 0.03 mol of potassium bicarbonate are introduced into an Erlenmeyer flask containing 150 ml of tetrahydrofuran. The mixture is brought to reflux for 24 hours. The reaction is brought to an end and, after cooling, the solution is filtered and evaporated under reduced pressure. The residue is then purified by chromatography, on a column of silica gel, methylene chloride generally being used as eluent. The final product is thus obtained in the base form.

Characteristics:

Molecular mass for C$_{22}$H$_{24}$N$_2$O$_3$.2HCl: 437 g.mol$^{-1}$

Yield: 80%

R$_f$: 0.62 (Ethanol)

Melting point: 246° C.

Infrared spectroscopy (KBr, ν cm$^{-1}$):

3010, 3000, 2980, 2965 (CH, CH$_2$, CH$_3$), 2650–2250 (NH$^+$), 1600 (C=C).

$^1$H Nuclear magnetic resonance (d$_6$-D.M.S.O., δ ppm):
3.15 (m, 8H, piperazine), 3.95 (s, 2H, C$\underline{H}_2$—N), 3.89 (s, 3H, O—C$\underline{H}_3$), 4.32 (s, 2H, C$\underline{H}_2$Ar), 6.45 (s, 1 H, CO—C$\underline{H}$), 6.92–7.87 (m, 8H, aromatic protons), 11.2 (broad s, 2H, 2N $\underline{H}^+$).

EXAMPLE 4

1-[(2,3-DIHYDROBENZOFUR-2-YL) METHYL]-4-BENZYLPIPERAZINE

By carrying out the preparation in the same way as in Example 1, but starting from 0.03 mol of 2-bromomethyl-2,3-dihydrobenzofuran, the title compound is obtained.

Characteristics:

Molecular mass for C$_{20}$H$_{24}$N$_2$O.2HCl: 381 g.mol$^{-1}$

Yield: 82%

R$_f$: 0.76 (Ethanol)

Melting point: 246° C.

Infrared spectroscopy (KBr, ν cm$^{-1}$):

3100, 3000, 2925 (CH, CH$_2$), 2650–2210 (N$^+$H), 1595 (C=C).

$^1$H Nuclear magnetic resonance (d$_6$-D.M.S.O., δ ppm):
3.02 (m, 2H, C$\underline{H}_2$—CH—CH$_2$—N), 3.50 (m, 10H, piperazine and CH$_2$—CH—C$\underline{H}_2$—N), 4.43 (s, N—C $\underline{H}_2$—Ar), 5.33 (m, $^1$H, CH$_2$—C$\underline{H}$—CH$_2$—N), 6.88–7.70 (m, 9H, aromatic protons).

EXAMPLE 5

1-[(5-METHOXYCHROMAN-3-YL) METHYL]-4-BENZYLPIPERAZINE (base and hydrochloride)

Stage A: 1-[(5-methoxychroman-3-yl)carbonyl]-4-benzylpiperazine hydrochloride

By carrying out the preparation as in Example 2 (Stage A), but replacing the chloride of chroman-2-carboxylic acid with the chloride of 5-methoxychroman-3-carboxylic acid, the title product is obtained.

Characteristics:
Molecular mass for $C_{22}H_{26}N_2O_3 \cdot HCl$: 402.5 g.mol$^{-1}$
Yield: 63%
$R_f$: 0.80 (Ethanol)
Melting point: 237° C.
Infrared spectroscopy (KBr, ν cm$^{-1}$):
3000, 2916, 2836 (CH, CH$_2$, CH$_3$), 2668–2331 (NH$^+$), 1635 (CO), 1603 (C=C).
$^1$H Nuclear magnetic resonance (d$_6$-D.M.S.O., δ ppm):
2.84 (m, 3H, Ar—C$\underline{H}_2$ and C$\underline{H}$—CO), 3.28 (m, 8H, C$\underline{H}_2$N), 3.88 (s, 3H.OC$\underline{H}_3$), 4.39 (m, 2H, OC$\underline{H}_2$), 4.60 (m, 2H, C$\underline{H}_2$—Ar), 6.51–7.72 (m, 8H, Ar), 11.64 (broad s, 1H, N$\underline{H}^+$).

Stage B: 1-[(5-METHOXYCHROMAN-3-YL)METHYL]-4-BENZYLPIPERAZINE (base and hydrochloride)

By carrying out the preparation as in Example 1, but replacing 1-[(5-fluoro-2,3-dihydrobenzofur-2-yl) carbonyl]-4-benzylpiperazine with the hydrochloride of 1-[(5-methoxychroman-3-yl) carbonyl]-4-benzylpiperazine obtained in Stage A, the title product is obtained.
Characteristics:
Molecular mass for $C_{22}H_{28}N_2O_2$: 352 g.mol$^{-1}$
Yield: 42%
$R_f$: 0.60 (Ethyl acetate)
Infrared spectroscopy (KBr, ν cm$^{-1}$):
3020, 2980, 2900, 2800 (CH, CH$_2$, CH$_3$), 1600 (C=C).
$^1$H Nuclear magnetic resonance (d$_6$-D.M.S.O., δ ppm):
2.82–3.20 (m, 13H, C$\underline{H}_2$—N), 3.41 (s, 2H, N—C$\underline{H}_2$—Ar), 3.89 (s, 3H, O—C$\underline{H}_3$), 4.27 (m, 2H, CH$_2$—CH—C$\underline{H}_2$—O), 7.31–6.37 (m, 8H, aromatic protons)
Hydrochloride:
Characteristics:
Molecular mass for $C_{22}H_{28}N_2O_2 \cdot 2HCl$: 425 g.mol$^{-1}$
Yield: 85%
$R_f$: 0.79 (Ethanol)
Melting point: 240° C.
Infrared spectroscopy (KBr, ν cm$^{-1}$):
3040, 2990, 2870, 2800 (CH, CH$_2$, CH$_3$), 2500–2400 (NH$^+$), 1610–1600 (C=C).

EXAMPLE 6

1-[(5-METHOXYCHROM-3-EN-3-YL)METHYL]-4-BENZYLPIPERAZINE (Base and hydrochloride)

Stage A: 1-[(5-Methoxychrom-3-en-3-yl)carbonyl]-4-benzylpiperazine hydrochloride By carrying out the preparation as in Example 2 (Stage A), but replacing the chloride of chroman-2-carboxylic acid with the chloride of 5-methoxychrom-3-ene-3-carboxylic acid, the title product is obtained.
Characteristics:
Molecular mass for $C_{22}H_{24}N_2O_3 \cdot HCl$: 400.5 g.mol$^{-1}$
Yield: 71%
$R_f$: 0.57 (Ethyl acetate)
Melting point: 234° C.
Infrared spectroscopy (KBr, ν cm$^{-1}$):
3110, 3025, 2990, 2950 (CH, CH$_2$, CH$_3$), 2657–2461 (NH$^+$), 1645 (CO), 1610 (C=C).
$^1$H Nuclear magnetic resonance (d$_6$-D.M.S.O., δ ppm):
3.42 (m, 8H, C$\underline{H}_2$N), 3.81 (m, 3H, OC$\underline{H}_3$), 4.31 (s, 2H, N-C$\underline{H}_2$—Ar), 4.23 (s, 1H, C$\underline{H}$—C—CO), 4.74 (s, 2H, C$\underline{H}_2$—O), 6.47 to 7.64 (m, 8H, Ar), 11.68 (broad s, 1H, N$\underline{H}^+$).

Stage B: 1-[(5-Methoxychrom-3-en-3-yl)methyl]-4-benzylpiperazine (Base and hydrochloride)

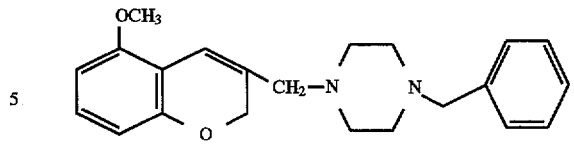

By carrying out the preparation as in Example 1, but replacing 1-[(5-fluoro-2,3-dihydrobenzofur-2-yl) carbonyl]-4-benzylpiperazine with the 1-[(5-methoxychrom-3-en-3-yl) carbonyl]-4-benzylpiperazine hydrochloride in the preceding stage, the title product is obtained.
Characteristics:
Molecular mass for $C_{22}H_{26}N_2O_2$: 350 g.mol$^{-1}$
Yield: 61%
$R_f$: 0.69 (Ethyl acetate)
Melting point: 95° C.
Infrared spectroscopy (KBr, ν cm$^{-1}$):
2970, 2930, 2810, 2795 (CH, CH$_2$, CH$_3$), 1610 (C=C).
$^1$H Nuclear magnetic resonance (d$_6$-D.M.S.O., δ ppm):
2.46 (m, 8H, piperazine), 3.06 (s, 2H, C$\underline{H}_2$—N), 3.51 (s, 2H, C$\underline{H}_2$—Ar), 3.80 (s, 3H, O—C$\underline{H}_3$), 4.70 (s, 2H, O—C$\underline{H}_2$), 6.39–7.32 (m, 9H, aromatic protons and H$_4$).
Hydrochloride:
Characteristics:
Molecular mass for $C_{22}H_{26}N_2O_2 \cdot 2HCl$: 423 g.mol$^{-1}$
Yield: 85%
$R_f$: 0.80 (Ethanol)
Melting point: 216° C.
Infrared spectroscopy (KBr, ν cm$^{-1}$):
2970, 2930, 2810, 2795 (CH, CH$_2$, CH$_3$), 1610 (C=C), 2550–2225 (NH$^+$).

EXAMPLE 7

1-(2-PHENOXYPROPIONYL)-4-BENZYLPIPERAZINE HYDROCHLORIDE

By carrying out the preparation as in Example 2 (Stage A), but replacing the chloride of chroman-2-carboxylic acid with the chloride of 2-phenoxypropionic acid, the title product is obtained.
Characteristics:
Molecular mass for $C_{20}H_{24}N_2O_2 \cdot HCl$: 360.5 g.mol$^{-1}$
Yield: 82%
$R_f$: 0.78 (Ethanol)
Melting point: 258° C.
Infrared spectroscopy (KBr, ν cm$^{-1}$):
3075, 2990, 2950 (CH, CH$_2$, CH$_3$), 2600–2750 (NH$^+$), 1665 (CO), 1610 (C=C).
$^1$H Nuclear magnetic resonance (d$_6$-D.M.S.O., δ ppm):
3.47 (m, 10H, C$\underline{H}_2$N and N—C$\underline{H}_2$—Ar), 4.47 (m, 3H, C$\underline{H}_3$), 5.37 (m, $^1$H, O—C$\underline{H}$—CO), 6.90–7.68 (m, 10H, Ar), 11.11 (broad s, $^1$H, N$\underline{H}^+$).

EXAMPLE 8

1-(2-PHENOXYBUTYRYL)-4-BENZYLPIPERAZINE HYDROCHLORIDE

By carrying out the preparation as in Example 2 (Stage A), but replacing the chloride of chroman-2-carboxylic acid with the chloride of 2-phenoxybutyric acid, the title product is obtained.
Characteristics:
Molecular mass for $C_{21}H_{26}N_2O_2 \cdot HCl$: 374.5 g.mol$^{-1}$
Yield: 39%
$R_f$: 0.82 (Ethanol)
Melting point: 210° C.
Infrared spectroscopy (KBr, ν cm$^{-1}$):

3005, 2850, 2810 (CH, $CH_2$, $CH_3$), 2500–2750 ($NH^+$), 1675 (CO), 1610, 1595 (C=C).

$^1$H Nuclear magnetic resonance ($d_6$-D.M.S.O., δ ppm):
1.13 (t, 3H, $CH_2$—$CH_3$), 1.89 (q, 2H, $CH_2$—$CH_3$), 3.55 (m, 8H, $CH_2$—N), 4.44 (s, 2H, $CH_2$—Ar), 5.15 (t, $^1$H, C$H$—$C_2H_5$), 6.94–7.74 (m, 10H, Ar), 12.04 (broad s, $^1$H, N$H^+$).

EXAMPLE 9

1-(2-PHENOXYPROPYL)-4-BENZYLPIPERAZINE (Hydrochloride and base)

By carrying out the preparation as in Example 1, but replacing 1-[(5-fluoro-2,3-dihydrobenzofur-2-yl) carbonyl]-4-benzylpiperazine with the 1-(2-phenoxypropionyl)-4-benzylpiperazine hydrochloride obtained in Example 7, the title product is obtained.

Characteristics:
Molecular mass for $C_{20}H_{26}N_2O_2$: 310 g.mol$^{-1}$
Yield: 40%
$R_f$: 0.42 (Ethyl acetate)
Infrared spectroscopy (KBr, ν cm$^{-1}$):
3145, 3010, 2885, 2840, 2815 (CH, $CH_2$, $CH_3$), 1605 (C=C).

$^1$H Nuclear magnetic resonance (CDCl$_3$, δ ppm):
1.27 (d, 3H, $CH_3$—CH), 3.51 (m, 10H, $CH_2$N and 8H, piperazine), 3.47 (s, 2H, $CH_2$—Ar), 4.52 (q, 1H, CH—$CH_3$), 6.84–7.30 (m, 10H, aromatic protons).

Hydrochloride:
Characteristics:
Molecular mass for $C_{20}H_{26}N_2O_2$.2HCl: 383 g.mol$^{-1}$
Yield: 77%
$R_f$: 0.91 (Ethyl acetate)
Melting point: 203° C.
Infrared spectroscopy (KBr, ν cm$^{-1}$):
3095, 3020, 3000, 2975 (CH, $CH_2$, $CH_3$), 2650–2200 ($NH^+$), 1605 (C=C).

$^1$H Nuclear magnetic resonance ($d_6$-D.M.S.O., δ ppm):
1.23 (d, 3H, $CH_3$—CH), 3.51 (m, 10H, $CH_2$N and 8H, piperazine), 4.36 (s, 2H, $CH_2$—Ar), 5.03 (q, 1H, C$H$—$CH_3$), 6.95–7.64 (m, 10H, aromatic protons).

EXAMPLE 10

1-(2-PHENOXYBUTYL)-4-BENZYLPIPERAZINE (Base and hydrochloride)

By carrying out the preparation as in Example 1, but replacing 1-[(5-fluoro-2,3-dihydrobenzofur-2-yl) carbonyl]-4-benzylpiperazine with the 1-(2-phenoxybutyryl)-4-benzylpiperazine hydrochloride obtained in Example 8, the title product is obtained.

Characteristics:
Molecular mass for $C_{21}H_{28}N_2O_2$: 324 g.mol$^{-1}$
$R_f$: 0.56 (Ethyl acetate)
Infrared spectroscopy (KBr, ν cm$^{-1}$):
3150, 3125, 2975, 2810, 2815 (CH, $CH_2$, $CH_3$), 1600 (C=C).

$^1$H Nuclear magnetic resonance (CDCl$_3$, δ ppm):
0.94 (t, 3H, $CH_2$—$CH_3$), 1.70 (q, 2H, $CH_2$—$CH_3$), 2.43–2.70 (m, 10H, $CH_2$—N+8H, piperazine), 3.46 (s, 2H, $CH_2$—Ar), 4.26–4.37 (m, $^1$H, CH—$CH_2$—N), 6.84–7.30 (m, 10H, aromatic protons).

Hydrochloride:
Molecular mass for $C_{21}H_{28}N_2O_2$.HCl: 397 g.mol$^{-1}$
Yield: 88%
$R_f$: 0.81 (Ethanol)
Melting point: 229° C.
Infrared spectroscopy (KBr, ν cm$^{-1}$):
3095, 3020, 3000, 2975 (CH, $CH_2$, $CH_3$), 2650–2200 ($NH^+$), 1605 (C=C).

$^1$H Nuclear magnetic resonance (CDCl$_3$, δ ppm):
0.92 (t, 3H, $CH_2$—$CH_3$), 1.64 (q, 2H, $CH_2$—$CH_3$), 3.45 (m, 10H, $CH_2$—N+8H, piperazine), 4.32 (s, 2H, C$H_2$—Ar), 4.87 (m, $^1$H, C$H$—$CH_2$—N), 6.94–7.59 (m, 10H, aromatic protons), 11.70 (broad s, 2H, 2N$H^+$).

EXAMPLE 11

1-[(7-METHOXY-2-OXOCHROM-3-EN-4-YL) METHYL]-4-(4-METHOXYBENZYL)PIPERAZINE 0.01 mol of 1-(4-methoxybenzyl)piperazine and 0.01 mol of 4-bromomethyl-7-methoxy-2-oxochrom-3-ene are introduced into an Edenmeyer flask containing 100 ml of tetrahydrofuran. The mixture is stirred at room temperature for 3 hours. 0.01 mol of potassium carbonate is then added and the mixture is brought to reflux. The reaction is monitored by thin layer chromatography. When it is finished, the solution is filtered and evaporated under reduced pressure. The residue is then purified by chromatography on a column of silica gel with methylene chloride and then ethyl acetate as eluents. The product is thus obtained in the base form.

Characteristics:
Yield: 45%
Melting point: 108° C.
Infrared spectroscopy (KBr, ν cm$^{-1}$):
3100–2980 (CH), 2850–2800 ($CH_2$, $CH_3$), 1715 (COO), 1610 (C=C).

$^1$H Nuclear magnetic resonance (CDCl$_3$, δ ppm):
2.50 (m, 8H, $CH_2$N), 3.45 (s, 2H $C_6H_4$—$CH_2$), 3.52 (s, 2H, Ar—$CH_2$), 3.79 (s, 3H OC$H_3$), 3.85 (s, 3H OC$H_3$), 6.15 (s, $^1$H, $H_3$), 6.85 (m, 4H, α of the OCH$_3$ groups), 7.20 (α, 2H, β of the OCH$_3$ groups, J=8 Hz), 7.70 (α, 1H, $H_5$, J=8 Hz).

Production of the hydrochloride
The base (0.002 mol) is dissolved in 10 ml of hot isopropanol. After dissolving, 5 ml of an isopropanol solution of hydrochloric acid are poured in. After cooling, the product is filtered and dried.
Characteristics:
Yield: 83%
Melting point: 208° C.

EXAMPLE 12

1-(2-PHENOXY-2-METHYLPROPIONYL)-4-BENZYLPIPERAZINE

A solution of 0.01 mol of 2-phenoxyisobutyric acid chloride (obtained by reaction of thionyl chloride with 2-phenoxyisobutyric acid) in 100 ml of methylene chloride is introduced into an Erlenmeyer flask containing a solution of 0.01 mol of 1-benzylpiperazine in 100 ml of methylene chloride. The mixture is stirred for 5 hours at room temperature, filtered and evaporated to dryness. The residue is taken up in water, basified and extracted with chloroform. The organic phases are combined, dried and evaporated.

EXAMPLE 13

1-(2-PHENOXY-2-METHYLPROPYL)-4-BENZYLPIPERAZINE 1 g of lithium aluminum hydride is added to 0.01 mol of the product obtained in the preceding Example 12, dissolved in 100 ml of tetrahydrofuran. The operation is repeated three hours later. After the end of the reaction, monitored by thin layer chromatography, the excess hydride is destroyed with 20 ml of methanol. After the evaporation to dryness, the residue is taken up in 5 ml of water and in 100 ml of ethyl acetate. The organic phase is filtered, evaporated and purified by chromatography on a column of silica gel, methylene chloride and ethyl acetate being used as eluent. The product is thus obtained in the base form.

Characteristics:
Yield: 33%
Infrared spectroscopy (KBr, v cm$^{-1}$):
3100–3000 (CH), 2970–2810 (CH$_2$—CH$_3$), 1591 (C=C).
$^1$H Nuclear magnetic resonance (CDCl$_3$, δ ppm):
1.26 (singlet, 6H, 2CH$_3$), 3.50 (singlet, 2H, Ar—CH$_2$—N)

Production of the hydrochloride
0.01 mol of base obtained is dissolved in 10 ml of hot isopropanol. After dissolving, 5 ml of an isopropanol solution of hydrochloric acid are poured in. After cooling, the product is filtered and dried.

Characteristics:
Yield: 86%
Melting point: 189° C.

EXAMPLE 14

1-[2-(4-CHLOROPHENOXY)PROPIONYL]-4-BENZYLPIPERAZINE

By carrying out the preparation as in Example 12, but using the chloride of 2-(4-chlorophenoxy) propionic acid, the title product is obtained.

EXAMPLE 15

1-[2-(4-CHLOROPHENOXY)PROPYL]-4-BENZYLPIPERAZINE

By carrying out the preparation as in Example 13, but using the 1-[2-(4-chlorophenoxy)propionyl]-4-benzylpiperazine obtained in Example 14, the title product is obtained.

EXAMPLE 16

1-[2-(4-CHLOROPHENOXY)-2-METHYLPROPIONYL]-4-BENZYLPIPERAZINE

By carrying out the preparation as in Example 12 (Stage A), but using the chloride of 2-(4-chlorophenoxy)-2-methylpropionic acid, the title product is obtained.

EXAMPLE 17

1-[2-(4-CHLOROPHENOXY)-2-METHYLPROPYL]-4-BENZYLPIPERAZINE

By carrying out the preparation as in Example 13, but using 1-[2-(4-chlorophenoxy)-2-methylpropionyl]-4-benzylpiperazine obtained in Example 16, the title product is obtained.

EXAMPLE 18

1-(2-PHENOXYPROPIONYL)-4-(4-METHOXYBENZYL)PIPERAZINE

By carrying out the preparation as in Example 12 (Stage A), but using the chloride of 2-phenoxypropionic acid and 1-(4-methoxybenzyl)piperazine, the title product is obtained.

EXAMPLE 19

1-(2-PHENOXYPROPYL)-4-(4-METHOXYBENZYL)PIPERAZINE

By carrying out the preparation as in Example 13, but using 1-(2-phenoxypropionyl)-4-(4-methoxybenzyl) piperazine obtained in Example 18, the title product is obtained.

EXAMPLE 20

1-(2-PHENOXY-2-METHYLPROPIONYL)-4-(4 METHOXYBENZYL)PIPERAZINE

By carrying out the preparation as in Example 12, but using the chloride of 2-phenoxy-2-methylpropionic acid and 1-(4-methoxybenzyl)piperazine, the title product is obtained.

EXAMPLE 21

1-(2-PHENOXY-2-METHYLPROPYL)-4-(4-METHOXYBENZYL)PIPERAZINE

By carrying out the preparation as in Example 13, but using 1-(2-phenoxy-2-methylpropionyl)-4-(4-methoxybenzyl)piperazine obtained in Example 20, the title product is obtained.

EXAMPLES 22 TO 55

By carrying out the preparation as in Example 2 (Stage A), but replacing the chloride of chroman-2-carboxylic acid with the appropriate acid chloride, the products of the following examples are obtained:

EXAMPLE 22: 1-[2-(3-FLUOROPHENOXY) PROPIONYL]-4-BENZYLPIPERAZINE

EXAMPLE 23: 1-[2-(2,4-DIETHYLPHENOXY) PROPIONYL]-4-BENZYLPIPERAZINE

EXAMPLE 24: 1-[2-(2-METHYL-4-ISOPROPYLPHENOXY)PROPIONYL]-4-BENZYL PIPERAZINE

EXAMPLE 25: 1-[2-(4-TRIFLUOROMETHYLPHENOXY)PROPIONYL]-4-BENZYL PIPERAZINE

EXAMPLE 26: 1-[2-(3-ETHYLPHENOXY)PROPIONYL] -4-BENZYLPIPERAZINE

EXAMPLE 27: 1-[2-(4-ETHYLPHENOXY)PROPIONYL] -4-BENZYLPIPERAZINE

EXAMPLE 28: 1-[2-(4-ETHOXYPHENOXY) PROPIONYL]-4-BENZYLPIPERAZINE

EXAMPLE 29: 1-[2-(4-PROPOXYPHENOXY) PROPIONYL]-4-BENZYLPIPERAZINE

EXAMPLE 30: 1-[2-(2-METHYL-4-SEC-BUTYLPHENOXY)PROPIONYL]-4-BENZYL PIPERAZINE

EXAMPLE 31: 1-[2-(4-ISOPROPYLPHENOXY) PROPIONYL]-4-BENZYLPIPERAZINE

EXAMPLE 32: 1-[2-(3-BROMOPHENOXY)-2-METHYLPROPIONYL]-4-BENZYL PIPERAZINE

EXAMPLE 33: 1-[2-(4-ETHOXYPHENOXY)-2-METHYLPROPIONYL]-4-BENZYL PIPERAZINE

EXAMPLE 34: 1-[2-(2,4-DICHLOROPHENOXY)-2-METHYLPROPIONYL]-4-BENZYL PIPERAZINE

EXAMPLE 35: 1-[2-(3-TRIFLUOROMETHYLPHENOXY)BUTYRYL]-4-BENZYL PIPERAZINE

EXAMPLE 36: 1-[2-(4-TERT-BUTYLPHENOXY) BUTYRYL]-4-BENZYLPIPERAZINE

EXAMPLE 37: 1-[2-(3-ISOPROPYLPHENOXY) BUTYRYL]-4-BENZYLPIPERAZINE

EXAMPLE 38: 1-[2-(4-FLUOROPHENOXY)BUTYRYL] -4-BENZYLPIPERAZINE

EXAMPLE 39: 1-[2-(3-IODOPHENOXY)BUTYRYL]-4-BENZYLPIPERAZINE

EXAMPLE 40: 1-[2-(2,4-DIIODOPHENOXY)BUTYRYL] -4-BENZYLPIPERAZINE

EXAMPLE 41: 1-[2-(2,4-DICHLOROPHENOXY) BUTYRYL]-4-BENZYLPIPERAZINE

EXAMPLE 42: 1-[2-(4-BROMOPHENOXY)BUTYRYL]-4-BENZYLPIPERAZINE
EXAMPLE 43: 1-[2-(4-METHYLPHENOXY)BUTYRYL]-4-BENZYLPIPERAZINE
EXAMPLE 44: 1-[2-(2-TRIFLUOROMETHYL-4-FLUOROPHENOXY)BUTYRYL]-4-BENZYLPIPERAZINE
EXAMPLE 45: 1-[2-(3-CHLOROPHENOXY)-2-METHYLBUTYRYL]-4-BENZYL PIPERAZINE
EXAMPLE 46: 1-(2-PHENOXYPENTANOYL)-4-BENZYLPIPERAZINE
EXAMPLE 47: 1-(2-PHENOXY-2-METHYLPENTANOYL)-4-BENZYLPIPERAZINE
EXAMPLE 48: 1-[2-(4-CHLOROPHENOXY)PENTANOYL]-4-BENZYLPIPERAZINE
EXAMPLE 49: 1-[2-(4-CHLOROPHENOXY)-2-METHYLPENTANOYL]-4-BENZYL PIPERAZINE
EXAMPLE 50: 1-[2-(4-HEXYLPHENOXY)PENTANOYL]-4-BENZYLPIPERAZINE
EXAMPLE 51: 1-[2-(3-CHLOROPHENOXY)PENTANOYL]-4-BENZYLPIPERAZINE
EXAMPLE 52: 1-(2-PHENOXYHEXANOYL)-4-BENZYLPIPERAZINE
EXAMPLE 53: 1-[2-(3,4-DICHLOROPHENOXY)HEXANOYL]-4-BENZYLPIPERAZINE
EXAMPLE 54: 1-[2-(4-METHOXYPHENOXY)HEPTANOYL]-4-BENZYLPIPERAZINE
EXAMPLE 55: 1-(2-PHENOXYOCTANOYL)-4-BENZYLPIPERAZINE

EXAMPLES 56 TO 89

By reducing as in Example 1, but using, at the start, the compounds of Examples 22 to 55, the following products are respectively obtained:

EXAMPLE 56: 1-[2-(3-FLUOROPHENOXY)PROPYL]-4-BENZYLPIPERAZINE
EXAMPLE 57: 1-[2-(2,4-DIETHYLPHENOXY)PROPYL]-4-BENZYLPIPERAZINE
EXAMPLE 58: 1-[2-(2-METHYL-4-ISOPROPYLPHENOXY)PROPYL]-4-BENZYL PIPERAZINE
EXAMPLE 59: 1-[2-(4-TRIFLUOROMETHYLPHENOXY)PROPYL]-4-BENZYL PIPERAZINE
EXAMPLE 60: 1-[2-(3-ETHYLPHENOXY)PROPYL]-4-BENZYLPIPERAZINE
EXAMPLE 61: 1-[2-(4-ETHYLPHENOXY)PROPYL]-4-BENZYLPIPERAZINE
EXAMPLE 62: 1-[2-(4-ETHOXYPHENOXY)PROPYL]-4-BENZYLPIPERAZINE
EXAMPLE 63: 1-[2-(4-PROPOXYPHENOXY)PROPYL]-4-BENZYLPIPERAZINE
EXAMPLE 64: 1-[2-(2-METHYL-4-SEC-BUTYLPHENOXY)PROPYL]-4-BENZYL PIPERAZINE
EXAMPLE 65: 1-[2-(4-ISOPROPYLPHENOXY)PROPYL]-4-BENZYLPIPERAZINE
EXAMPLE 66: 1-[2-(3-BROMOPHENOXY)-2-METHYLPROPYL]-4-BENZYLPIPERAZINE
EXAMPLE 67: 1-[2-(4-ETHOXYPHENOXY)-2-METHYLPROPYL]-4-BENZYLPIPERAZINE
EXAMPLE 68: 1-[2-(2,4-DICHLOROPHENOXY)-2-METHYLPROPYL]-4-BENZYL PIPERAZINE
EXAMPLE 69: 1-[2-(3-TRIFLUOROMETHYLPHENOXY)BUTYL]-4-BENZYLPIPERAZINE
EXAMPLE 70: 1-[2-(4-TERT-BUTYLPHENOXY)BUTYL]-4-BENZYLPIPERAZINE
EXAMPLE 71: 1-[2-(3-ISOPROPYLPHENOXY)BUTYL]-4-BENZYLPIPERAZINE
EXAMPLE 72: 1-[2-(4-FLUOROPHENOXY)BUTYL]-4-BENZYLPIPERAZINE
EXAMPLE 73: 1-[2-(3-IODOPHENOXY)BUTYL]-4-BENZYLPIPERAZINE
EXAMPLE 74: 1-[2-(2,4-DIIODOPHENOXY)BUTYL]-4-BENZYLPIPERAZINE
EXAMPLE 75: 1-[2-(2,4-DICHLOROPHENOXY)BUTYL]-4-BENZYLPIPERAZINE
EXAMPLE 76: 1-[2-(4-BROMOPHENOXY)BUTYL]-4-BENZYLPIPERAZINE
EXAMPLE 77: 1-[2-(4-METHYLPHENOXY)BUTYL]-4-BENZYLPIPERAZINE
EXAMPLE 78: 1-[2-(2-TRIFLUOROMETHYL-4-FLUOROPHENOXY)BUTYL]-4-BENZYLPIPERAZINE
EXAMPLE 79: 1-[2-(3-CHLOROPHENOXY)-2-METHYLBUTYL]-4-BENZYLPIPERAZINE
EXAMPLE 80: 1-(2-PHENOXYPENTYL)-4-BENZYLPIPERAZINE
EXAMPLE 81: 1-(2-PHENOXY-2-METHYLPENTYL)-4-BENZYLPIPERAZINE
EXAMPLE 82: 1-[2-(4-CHLOROPHENOXY)PENTYL]-4-BENZYLPIPERAZINE
EXAMPLE 83: 1-[2-(4-CHLOROPHENOXY)-2-METHYLPENTYL]-4-BENZYLPIPERAZINE
EXAMPLE 84: 1-[2-(4-HEXYLPHENOXY)PENTYL]-4-BENZYLPIPERAZINE
EXAMPLE 85: 1-[2-(3-CHLOROPHENOXY)PENTYL]-4-BENZYLPIPERAZINE
EXAMPLE 86: 1-(2-PHENOXYHEXYL)-4-BENZYLPIPERAZINE
EXAMPLE 87: 1-[2-(3,4-DICHLOROPHENOXY)HEXYL]-4-BENZYLPIPERAZINE
EXAMPLE 88: 1-[2-(4-METHOXYPHENOXY)HEPTYL]-4-BENZYLPIPERAZINE
EXAMPLE 89: 1-(2-PHENOXYOCTYL)-4-BENZYLPIPERAZINE
EXAMPLE 90: 1-[(5-FLUOROCHROMAN-2-YL)METHYL]-4-BENZYLPIPERAZINE

By carrying out the preparation as in Example 1, but using, at the start, 1-[(5-fluorochroman-2-yl) carbonyl]-4-benzylpiperazine resulting from the condensation of 5-fluorochroman-2-carboxylic acid with N-benzylpiperazine, the title compound is obtained.

EXAMPLE 91: 1-[(CHROM-3-EN-2-YL)METHYL]-4-BENZYLPIPERAZINE

By carrying out the preparation as in Example 1, but using, at the start, 1-[(chrom-3-en-2-yl) carbonyl]-4-benzylpiperazine resulting from the condensation of chrom-3-ene-2-carboxylic acid with N-benzylpiperazine, the title compound is obtained.

EXAMPLES 92 TO 106

By carrying out the preparation as in Example 2, but replacing 1-benzylpiperazine with the appropriate piperazine, the following products are obtained:

EXAMPLE 92: 1-[(CHROMAN-2-YL)METHYL]-4-(4-METHOXYBENZYL)PIPERAZINE
EXAMPLE 93: 1-[(CHROMAN-2-YL)METHYL]-4-(2-METHOXYBENZYL)PIPERAZINE
EXAMPLE 94: 1-[(CHROMAN-2-YL)METHYL]-4-(3-METHOXYBENZYL)PIPERAZINE
EXAMPLE 95: 1-[(CHROMAN-2-YL)METHYL]-4-(4-HYDROXYBENZYL)PIPERAZINE
EXAMPLE 96: 1-[(CHROMAN-2-YL)METHYL]-4-(4-ISOPROPOXYBENZYL) PIPERAZINE

EXAMPLE 97: 1-[(CHROMAN-2-YL)METHYL]-4-(4-TRIFLUOROMETHYLBENZYL) PIPERAZINE
EXAMPLE 98: 1-[(CHROMAN-2-YL)METHYL]-4-(4-METHYLBENZYL)PIPERAZINE
EXAMPLE 99: 1-[(CHROMAN-2-YL)METHYL]-4-(4-CHLOROBENZYL)PIPERAZINE
EXAMPLE 100: 1-[(CHROMAN-2-YL)METHYL]-4-(4-FLUOROBENZYL)PIPERAZINE
EXAMPLE 101: 1-[(CHROMAN-2-YL)METHYL]-4-(3,4-DICHLOROBENZYL) PIPERAZINE
EXAMPLE 102: 1-[(CHROMAN-2-YL)METHYL]-4-(2,4-DICHLOROBENZYL) PIPERAZINE
EXAMPLE 103: 1-[(CHROMAN-2-YL)METHYL]-4-(2,3,4-TRIMETHOXYBENZYL) PIPERAZINE
EXAMPLE 104: 1-[(CHROMAN-2-YL)METHYL]-4-(NAPHTHYLMETHYL)PIPERAZINE
EXAMPLE 105: 1-[(CHROMAN-2-YL)METHYL]-4-(PHENYLETHYL)PIPERAZINE
EXAMPLE 106: 1-[(CHROMAN-2-YL)METHYL]-4-(PHENYLBUTYL)PIPERAZINE

PHARMACOLOGICAL STUDY OF THE DERIVATIVES OF THE INVENTION

EXAMPLE A: STUDY OF THE ACUTE TOXICITY

The acute toxicity was assessed after oral administration to batches of 8 mice (26 ±2 grams) of a dose of 100 mg.kg$^{-1}$ of the compounds of the invention. The animals were observed at regular intervals during the first day and daily for the two weeks following the treatment.

It appears that the compounds of the invention are entirely nontoxic. They do not result in any deaths after administration at a dose of 100 mg.kg$^{-1}$ and disorders are not observed after administration of this dose.

EXAMPLE B: IN VITRO RECEPTOR AFFINITY ASSESSMENT

The products are tested on each receptor at 5 different concentrations ($10^{-5}$M, $10^{-6}$M, $10^{-7}$M, $10^{-8}$M and $10^{-9}$M) in triplicate. When the binding coefficient IC$_{50}$ (concentration of product which displaces 50% of the radioligand) is less than a concentration of $10^{-6}$M, the Ki is measured by using 12 concentrations of the product.

The receptors for which the affinity of the compounds of the invention was determined, the tissue chosen, the concentration used for determining the non-specific fraction and the radioligand used to label the receptor are shown in Table A.

TABLE A

In vitro receptor affinity assessment:

| Receptor or site | Radioligand | Non-specific fraction | Tissue |
|---|---|---|---|
| 5-HT$_{1A}$ | 8-OH-DPAT | $10^{-5}$M Buspirone | Hippocampus |
| 5-HT$_{1B}$ | [$^3$H]-Cyanopindolol | $10^{-5}$M Cold serotonin | Rat brain |
| 5-HT$_{1C}$ | N-methylmesulergine | $10^{-5}$M Mianserin | Frontal cortex Hippocampus |
| 5-HT$_2$ | [$^3$H]-Ketanserin | $10^{-5}$M Spiperone | Frontal cortex |
| 5-HT$_3$ | [$^3$H]-Quipazine | $10^{-5}$M Zacopride | Rat ileum |
| α$_1$ | [$^3$H]-Prazosin | $10^{-5}$M Phentolamine | Rat brain |
| α$_2$ | [$^3$H]-Rauwolscine | $10^{-5}$M Yohimbine | Rat brain |
| D$_1$ | [$^3$H]-SCH 23390 | $10^{-6}$M Butaclamol | Rat striatum |

TABLE A-continued

In vitro receptor affinity assessment:

| Receptor or site | Radioligand | Non-specific fraction | Tissue |
|---|---|---|---|
| D$_2$ | [$^3$H]-Raclopride | $10^{-6}$M Haloperidol | Rat striatum |
| M$_1$ | [$^3$H]-Telenzepine | $10^{-5}$M Atropine | Cortex |
| H$_1$ | [$^3$H]-Pyrilamine | $10^{-6}$M Chlorpheniramine | Calf cortex |
| σ | [$^3$H]-DTG or [$^3$H]-3-PPP | $10^{-6}$M 3-PPP | Calf hippocampus |
| σ$_1$ | [$^3$H]-Pentazocine | $5 \times 10^{-6}$M Haloperidol | Guinea pig brain |
| σ$_2$ | [$^3$H]-DTG | $5 \times 10^{-6}$M Haloperidol | Guinea pig brain |

The results of the tests have shown that the compounds of the invention are powerful and selective ligands of σ receptors. The examples of binding to σ receptors are given in Table B below.

TABLE B

Results of the test of binding to σ receptors:

| Compound | Receptor | Radioligand | IC$_{50}$(M) |
|---|---|---|---|
| Example 1 | σ | [$^3$H]-DTG | $9.1 \times 10^{-9}$ |
| Example 3 | σ | [$^3$H]-DTG | $1.3 \times 10^{-9}$ |
| Example 4 | σ | [$^3$H]-DTG | $7 \times 10^{-9}$ |
| Example 9 | σ | [$^3$H]-DTG | $4 \times 10^{-9}$ |
|  | σ$_1$ | [$^3$H]-Pentazocine | $1.3 \times 10^{-9}$ |
|  | σ$_2$ | [$^3$H]-DTG | $4 \times 10^{-8}$ |

EXAMPLE C: ANTAGONISM OF HYPERMOTILITY INDUCED BY AMPHETAMINE

This test was developed by Costall B., et al. (Brain Research, 1977, 123, 89–111).

Groups of 10 NMRI-CERJ mice are injected intraperitoneally (IP) with 4 mg.kg$^{-1}$ of d-amphetamine immediately after the compound to be tested (also injected by the IP route) and the mice are placed in an activity cage for 30 minutes.

The number of interruptions of photoelectric cells is recorded, as well as the stereotypical behavior.

The activity of the tested compounds is expressed as percentage of antagonism of the hyperactivity induced by amphetamine.

The results of the test show that the compounds of the invention are powerful antagonists of the hypermotility induced by amphetamine. Thus, for example, the compounds of Examples of 1 and 4, at a dose of 64 mg/kg, antagonize the hypermotility induced by amphetamine to 43% and to 61% respectively. The products of the invention are thus good candidates for the treatment of disorders of the central nervous system.

EXAMPLE D: ANTAGONISM OF THE HYPERACTIVITY INDUCED BY N-ALLYLNORMETAZOCINE

This test was developed by Snyder S. H. et al. (J. Neuropsychiatry, 1989, 1,7–15).

N-Allylnormetazocine ((+)-SKF 10047) induces psychotic behavior in man and is the prototype agonist for σ receptors.

Measurement of the hyperactivity induced by this product is therefore used as an alternative model for detecting the antipsychotic activity of the compounds which have an effect on σ receptors.

A group of 12 rats is treated with the compound to be tested before subcutaneous administration of 50 mg/kg of N-allylnormetazocine. 30 minutes later, the animals are placed in an activity cage for 30 minutes.

Haloperidol is used as reference compound.

The results of the tests show that the compounds of the invention are powerful antagonists of the hyperactivity induced by N-allylnormetazocine. Thus, for example, the compound of Example 9, at a dose of 32 mg.kg$^{-1}$, antagonizes the hypermotility induced by N-allylnormetazocine by 42%.

This test therefore confirms the advantage of the products of the invention in the treatment of disorders of the central nervous system.

EXAMPLE E: CATALEPTIGENIC EFFECT SEARCH

This test was developed by Chermat R. et al. (J. Pharmacol., 1975, 6,493–496).

6 groups of Wistar rats were injected intraperitoneally with the compounds of the invention. Cataleptigenic activity is looked for at intervals of 30 minutes. Prochlorperazine is used as reference.

The results of this test show that the compounds of the invention have a very weak cataleptigenic effect in comparison with prochlorperazine under the same test conditions. This result confirms the absence of side effects of extrapyramidal type of the products of the invention which could be expected following the results of the binding tests (Example B).

EXAMPLE F: STUDY OF THE ANTIDEPRESSANT ACTIVITY OF THE COMPOUNDS OF THE INVENTION

PRINCIPLE

The products are studied using the "learnt denial" model which consists in inducing in the animal, by a series of uncontrollable aversive events, a deficiency during subsequent avoidance tasks.

PROTOCOL

This test was developed by Sherman A. D., Sacquitne J. L. and Petty F. (Pharmacol. Blochem. Behav., 1982, 16, 449–454). Male Wistar rats with a weight of between 180 and 280 grams are used. The animals are kept in the animal house for 1 week before the test, in plastic boxes, in groups of 10, at an ambient temperature of 21 ° C.±1° C., with free access to water and food.

The animals are then isolated in small-sized boxes and are subjected to 60 unavoidable electric shocks (0.8 mA every minute±15 seconds). A group of control rats does not receive electric shocks.

The ability of the animals to learn to avoid shocks (passage from one compartment to the other, in order to avoid electrical shocks) is assessed 48 hours later and for three consecutive days. During the learning sessions, the animals are subjected to 2 tests per minute for 15 minutes. The number of failures to escape is recorded for each rat. The animals are treated (injection of 0.5 ml/100 g intraperitoneally), having been deprived of nourishment, 6 hours after the unavoidable shocks and 4 days running, in the morning, 30 minutes before the learning session, and in the evening, between 18:00 and 19:00.

The products studied are dissolved in distilled water.

The products studied are administered at doses of 0.05 mg/kg/day.

RESULTS

The test proves that some products of the invention significantly decrease the number of failures to escape, which reflects, for some products of the invention, a high antidepressant-type activity.

EXAMPLE G: STUDY OF THE ANXIOLYTIC ACTIVITY—SO-CALLED BRIGHT/DARK CAGES TEST IN MICE

PROTOCOL

This test was developed by Crawley et al. (Pharmacol. Blochem. Behav. 1981, 15 (5), 695–699), and then modified and behaviorally validated.

It involves two PVC cages of the same size (20×20×14 cm). One is strongly lit by a 100 W lamp ("cold" light) and the other is darkened. The two cages are separated from one another by means of a small opaque tunnel (5×7 cm). The mice are individually introduced into the dark cage. A record is made, using keyboards connected to a computer, for 5 minutes, of the time spent by the animals in the illuminated cage and the number of transitions between the dark cage and the illuminated cage. Each experimental group comprises a minimum of 15 animals.

RESULTS

The intraperitoneal administration of the products of the invention results in an increase in the time spent by the mice in the illuminated cage and in the number of transitions between the dark cage and the illuminated cage, This significant increase in the two parameters studied shows a remarkable anxiolytic activity of the compounds of the invention.

EXAMPLE H: SEARCH FOR AN ANTIARTHRITIC-TYPE ACTIVITY IN RATS

PROTOCOL

Groups of 5 male or female Lewis rats with a weight of 130 g to 150 g are used. A suspension of 0.3 mg of killed Mycobacterium tuberculosis in 0.1 ml of mineral oil (Complete Freund's Adjuvant, CFA) is administered in the region of the hind paw on Day 1. The sizes of the hind paws are measured by displacement of water on Days 0, 1, 5, 14 and 18. The products to be tested are placed in suspension in carboxymethyl cellulose and administered orally for 5 consecutive days, Days 1 to 5.

RESULTS

After administration of the products of the invention, a significant decrease in the size of the hind paws is observed in the early phase and in the late phase of inflammation (after Day 14). The products of the invention are therefore good candidates in the treatment of arthritis.

EXAMPLE I: PHARMACEUTICAL COMPOSITION

1. Tablets containing a charge of 0.1 mg of 1-[(5-methoxychroman-3-yl)methyl]-4-benzylpiperazine which can be used in the treatment of disorders of the central nervous system.

| Formula for 10,000 tablets: | |
|---|---|
| 1-[(5-Methoxychroman-3-yl)methyl]-4-benzylpiperazine | 1 g |
| Wheat starch | 75 g |
| Maize starch | 75 g |
| Lactose | 325 g |
| Magnesium stearate | 10 g |
| Silica | 5 g |
| Hydroxypropyl cellulose | 10 g |

2. Tablets containing a charge of 50 mg of 1-[(7-methoxy-2-oxochrom-3-en-4-yl) methyl]-4-(4-methoxybenzyl)

piperazine which can be used in the treatment of chronic arthritis.

| Formula for 1000 tablets: | |
|---|---|
| 1-[(7-Methoxy-2-oxochrom-3-en-4-yl)methyl]-4-(4-methoxybenzyl)piperazine | 50 g |
| Wheat starch | 150 g |
| Maize starch | 150 g |
| Lactose | 450 g |
| Magnesium stearate | 10 g |
| Silica | 5 g |
| Hydroxypropyl cellulose | 10 g |

We claim:

1. A compound selected from those of formula (I):

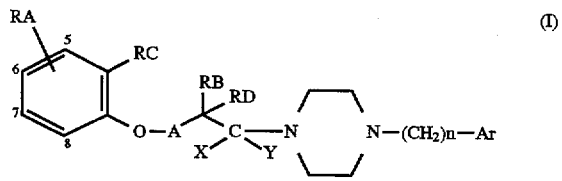

in which

Ar represents phenyl, naphthyl, substituted phenyl or substituted naphthyl, n represents an integer of 1 to 4 inclusive, RB and RC together form a —$(CH_2)_q$— bridge with q having the value 1 or 2 and, in this case, A represents a —$(CH_2)_p$— bridge with p representing 0, or 1 and such that p+q=2, and in this case RA represents hydroxyl or alkoxy situated in the 5-position of the aromatic ring which carries it or RA represents hydrogen or halogen, in any position on the aromatic ring, or RB and RC together form a —CH= bridge, and the bond which bonds it to the aromatic ring is single, and in this case A represents $CH_2$ and RA represents hydrogen, hydroxyl or alkoxy situated in the 5-position of the aromatic ring which carries it, or RB and RC together form a single bond and then A represents a group

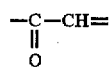

the carbonyl being bonded to the oxygen and the bond connecting A to the carbon carrying the side chain is double, and in this case RA represents hydrogen, hydroxyl or alkoxy, X and Y each represent hydrogen and RD, which only exists when all the bonds of the carbon which carries it are single, represents hydrogen, it being understood that, except when otherwise mentioned, the terms "alkyl" and "alkoxy" denote linear or branched saturated groups having 1 to 6 carbon atoms inclusive, the term "substituted" concerning the phenyl and naphthyl substituents means that the latter can be substituted by one to three groups chosen from hydroxyl, alkyl, alkyl substituted by one or a number of halogens, alkoxy and halogen, an optical isomer thereof in the pure form or in the form of a mixture, and an addition salt thereof with a pharmaceutically-acceptable acid or base.

2. A compound of claim 1 which is 1-[(chroman-2-yl)methyl)]-4-benzylpiperazine.

3. A compound of claim 1 which is 1-[(7-methoxy-2H-2-oxochrom-3-en-4-yl) methyl]-4-benzylpiperazine.

4. A compound of claim 1 which is 1-[(7-methoxy-2H-2-oxochrom-3-en-4-yl) methyl]-4-(4-methoxybenzyl) piperazine.

5. A pharmaceutical composition containing, as active principle, at least one compound of claim 1 in combination with one or a number of pharmaceutically-acceptable excipients.

6. A method of treating a mammal afflicted with a condition of the central nervous system selected from schizophrenia, anxiety, and depression, comprising the step of administering to the said mammal an amount of a compound of claim 1 which is effective for alleviating the said condition.

* * * * *

UNITED STATES PATENT AND TRADEMARK OFFICE
CERTIFICATE OF CORRECTION

PATENT NO. : 5,691,340
DATED : Nov. 25, 1997
INVENTOR(S) : G. Baziard-Monysset; S. Yonnes; Y. Labsulta; M. Payard; D.H. Caignard; P. Renard; M.C. Rettori It is certified that error appears in the above-identified patent and that said Letters Patent is hereby corrected as shown below:

Column 7, line 47: Delete "[" from the end of the line.
Column 7, line 48: Insert --[-- at the beginning of the line.
Column 12, line 14: "Edenmeyer" should read --Erlenmeyer--.

Signed and Sealed this

Seventeenth Day of February, 1998

Attest:

BRUCE LEHMAN

Attesting Officer      Commissioner of Patents and Trademarks